US012434022B2

(12) United States Patent
Bartels et al.

(10) Patent No.: US 12,434,022 B2
(45) **Date of Patent: *Oct. 7, 2025**

(54) INHALATION DEVICE AND METHOD

(71) Applicant: INVOX BELGIUM NV, Diepenbeek (BE)

(72) Inventors: Frank Bartels, Hattigen (DE); Jürgen Rawert, Cologne (DE)

(73) Assignee: INVOX BELGIUM NV, Diepenbeek (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/175,301

(22) Filed: Feb. 27, 2023

(65) Prior Publication Data

US 2023/0277784 A1 Sep. 7, 2023

Related U.S. Application Data

(63) Continuation of application No. 16/609,182, filed as application No. PCT/EP2018/061056 on Apr. 30, 2018, now Pat. No. 11,612,704.

(Continued)

(30) Foreign Application Priority Data

Apr. 28, 2017 (EP) .................................... 17168869

(51) Int. Cl.
*A61M 15/00* (2006.01)
*A61M 11/00* (2006.01)

(52) U.S. Cl.
CPC ...... *A61M 15/0086* (2013.01); *A61M 11/007* (2014.02); *A61M 15/0065* (2013.01);

(Continued)

(58) Field of Classification Search
CPC .. A61M 15/00; A61M 15/0086; A61M 11/00; A61M 11/007; A61M 15/0065;

(Continued)

(56) References Cited

U.S. PATENT DOCUMENTS 5,497,944 A 3/1996 Weston et al.
6,454,135 B1 9/2002 Brozell (Continued)

FOREIGN PATENT DOCUMENTS

JP 002630347 B 7/1997
JP H11-500646 A 1/1999

(Continued)

*Primary Examiner* — Rachel T Sippel
*Assistant Examiner* — Jacqueline M Pinderski
(74) *Attorney, Agent, or Firm* — Synergy IP Group AG

(57) ABSTRACT

The invention relates to the field of inhalation devices for liquids. In particular, the invention relates to an inhalation device having improved flow characteristics. A inhalation device for medically active liquids (F) for generation of an aerosol comprises a housing (1), inside this housing (1) a reservoir (2) for storing a liquid (F), a pumping device with a hollow cylinder (9) providing a pumping chamber (3) for the generation of a pressure inside said pumping chamber (3), wherein the pumping chamber is fluidically connected with the reservoir (2) via an inlet check valve (4) which blocks in direction of the reservoir (2), a riser pipe (5) which can be received with at least one reservoir-facing, interior end (5A) in said hollow cylinder (9), and a nozzle (6) which is connected liquid-tight to an exterior end (5B) of the riser pipe (5), wherein the volume of the pumping chamber (3) is changeable by means of relative motion of the cylinder (9) to the riser pipe (5), and is characterised in that the riser pipe (5) is immobile and firmly attached to the housing (1) and to the nozzle (6), whereas the hollow cylinder (9) is moveable relative to the housing (1) and to the nozzle (6). The (Continued)

invention also discloses a method for the generation of an aerosol of a medically active liquid (F) by means of an inhalation device.

20 Claims, 2 Drawing Sheets

Related U.S. Application Data

(60) Provisional application No. 62/491,965, filed on Apr. 28, 2017.

(52) U.S. Cl.
CPC ... *A61M 15/009* (2013.01); *A61M 2202/0468* (2013.01); *A61M 2205/3337* (2013.01); *A61M 2205/3351* (2013.01); *A61M 2205/3355* (2013.01); *A61M 2205/8281* (2013.01)

(58) Field of Classification Search
CPC ........ A61M 15/009; A61M 2202/0468; A61M 2205/3337; A61M 2205/3351; A61M 2205/3355; A61M 2205/8281; A61M 2205/276; B05B 11/1091; B05B 11/1004
See application file for complete search history.

(56) References Cited

U.S. PATENT DOCUMENTS

| | | | | |
|---|---|---|---|---|
| RE43,329 | E | 4/2012 | Py | |
| 8,539,946 | B2 | 9/2013 | Esteve et al. | |
| 11,612,704 | B2 * | 3/2023 | Bartels | A61M 15/0065 128/200.23 |
| 11,717,622 | B2 * | 8/2023 | Bartels | A61M 15/009 128/200.23 |
| 2002/0004138 | A1 | 1/2002 | Silverstein et al. | |
| 2002/0100772 | A1 | 8/2002 | Bonningue | |
| 2002/0134797 | A1 * | 9/2002 | Grimm | B05B 11/0005 222/205 |
| 2003/0078551 | A1 * | 4/2003 | Hochrainer | A61M 11/006 604/295 |
| 2004/0068222 | A1 | 4/2004 | Brian | |
| 2005/0039738 | A1 | 2/2005 | Zimlich et al. | |
| 2005/0081846 | A1 * | 4/2005 | Barney | A61M 15/008 128/200.23 |
| 2007/0095853 | A1 | 5/2007 | Bonney et al. | |
| 2007/0175469 | A1 | 8/2007 | Rohrschneider et al. | |
| 2009/0216183 | A1 | 8/2009 | Minotti | |
| 2011/0041844 | A1 * | 2/2011 | Dunne | B05B 1/26 128/203.12 |
| 2011/0290242 | A1 * | 12/2011 | Bach | A61M 15/0036 128/200.21 |
| 2012/0090603 | A1 * | 4/2012 | Dunne | A61M 11/06 128/200.22 |
| 2012/0091229 | A1 * | 4/2012 | Laidler | B05B 11/026 222/207 |
| 2012/0298694 | A1 | 11/2012 | Holzmann | |
| 2013/0199521 | A1 | 8/2013 | Hausmann et al. | |
| 2014/0076308 | A1 | 3/2014 | Dunne | |
| 2017/0014215 | A1 * | 1/2017 | Rahmel | A61M 15/0073 |
| 2017/0100551 | A1 | 4/2017 | Baldwin | |
| 2019/0178401 | A1 * | 6/2019 | Zaggl | F16K 17/02 |
| 2020/0009333 | A1 * | 1/2020 | Dunne | B05B 15/33 |
| 2021/0252234 | A1 * | 8/2021 | Bartels | A61M 11/007 |

FOREIGN PATENT DOCUMENTS

| | | | |
|---|---|---|---|
| JP | 2002-080081 | A | 3/2002 |
| JP | 2007-520349 | A | 7/2007 |
| JP | 2013-530781 | A | 8/2013 |
| JP | 2017-051786 | A | 3/2017 |
| WO | 96/40332 | A1 | 12/1996 |
| WO | WO 2003/103760 | | 12/2003 |
| WO | WO 2005/075105 | A1 | 8/2005 |
| WO | 2011/157561 | A1 | 12/2011 |
| WO | WO 2018/234527 | A1 | 12/2018 |

* cited by examiner

INHALATION DEVICE AND METHOD

CROSS-REFERENCE TO RELATED APPLICATIONS

This application is a continuation of U.S. application Ser. No. 16/609,182, filed Oct. 28, 2019, which is a United States Application under 35 U.S.C. § 371 claiming priority to and the benefit of PCT Application No. PCT/EP2018/061056, filed Apr. 30, 2018, which claims priority to and the benefit of European Application No. 17168869.0, filed on Apr. 28, 2017, and U.S. Provisional Application Ser. No. 62/491,965, filed on Apr. 28, 2017 the contents of each of which are hereby incorporated by reference in their entireties.

FIELD OF THE INVENTION

The invention relates to the field of inhalation devices for medically active liquids for inhalation therapy. In particular, the invention relates to an inhalation device having improved flow characteristics, and to methods for the generation of an aerosol of a medically active liquid by means of an inhalation device.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e. small liquid droplets embedded in a gas. Such an inhalation device is known e.g. from document EP 0 627 230 B1. Essential components of this inhalation device are a reservoir in which the liquid that is to be aerosolized is contained; a pumping device for generation of a pressure being sufficiently high for nebulizing; as well as an atomizing device in the form of a nozzle. By means of the pumping device, the liquid is drawn in a discrete amount, i.e. not continuously, from the reservoir, and fed to the nozzle. The pumping device works without propellant and generates pressure mechanically.

A known embodiment of such an inhalation device is presented in document WO 91/14468 A1. In such a device, the pressure in the pumping chamber which is connected to the housing is generated by movement of a moveable hollow piston. The piston is moveably arranged inside the immobile cylinder or pumping chamber. The (upstream arranged) inlet of the hollow piston is fluidically connected to the interior of the reservoir (reservoir pipe section). Its (downstream arranged) tip leads into the pumping chamber. Furthermore, a check valve that inhibits a back flow of liquid into the reservoir is arranged inside the tip of the piston.

For filling the piston, the same is directly connected with its upstream end to the reservoir. By pulling out the piston of the pumping chamber provided inside a hollow cylinder, its interior volume is enlarged, such that an increasing under pressure is built up inside the pumping chamber. This pressure propagates through the hollow piston into the reservoir, such that liquid is sucked from the same into the piston. At the same time, said valve opens at its tip, since the pressure inside the reservoir is higher than inside the (yet empty) pumping chamber. The pumping chamber is being filled. At the same time, a spring is loaded, and locked at the motion's end when the moveable piston has reached its lower dead centre (in the case of a vertically arranged device) and the pumping chamber is filled.

The spring can be manually unlocked. The stored energy is then abruptly released. The piston is again pushed in direction of the pumping chamber and into the same, thus decreasing its interior volume. The aforementioned check valve is now closed, such that a growing pressure builds up inside the pumping chamber, since the liquid is inhibited from flowing back into the reservoir. Eventually, this pressure results in ejection of the liquid from the nozzle which is arranged at the downstream end of the pumping chamber.

In order to face the risk of a reverse flow of already ejected liquid or even outside air, a further check valve, subsequently being called outlet valve, can be arranged at the downstream end of the pumping chamber just before the nozzle, allowing emitted liquid to pass, but blocking incoming gas or liquid.

The piston is arranged inside the pressure spring which is designed as helical spring, thus limiting its outside diameter. Also because of the typically small volume (e.g. 15 μl), the piston is designed with a thin interior (and often also exterior) diameter.

This typically small inner diameter of the moveable piston (e.g. 0.3 to 1.0 mm), together with a small size of the check valve being arranged within, is a drawback of the described construction. The small diameter results in a high flow resistance, such that in particular, media of higher viscosities flow into and through the piston only very slowly. In other words, the described construction is suitable especially for low-viscosity (aqueous) liquids and for emitting low doses thereof. Furthermore, fabrication of a sufficiently tight check valve of small diameter is difficult.

An object of the invention is the provision of a device that avoids the drawbacks of the known art. A further object is to provide an inhalation device that also allows for the delivery of a nebulised aerosol generated from a medically active liquid of higher viscosities in a short time, and with high reproducibility. Further objects will become apparent on the basis of the following descriptions, the drawings and the claims.

SUMMARY OF THE INVENTION

The objects are solved by the inhalation device provided according to the main claim, as well as by the method provided according to claim 9. Advantageous embodiments are described in the respective dependent claims, the subsequent description, as well as the accompanying figures.

In a first aspect, the invention provides a hand-held inhalation device for delivering a nebulised medically active aerosol for inhalation therapy, comprising (a) a housing having a user-facing side; (b) an impingement-type nozzle for generating the nebulised aerosol by collision of at least two liquid jets, the nozzle being firmly affixed to the user-facing side of the housing such as to be immobile relative to the housing; (c) a fluid reservoir arranged within the housing; and (d) a pumping unit arranged within the housing, the pumping unit having an upstream end that is fluidically connected to the fluid reservoir and a downstream end that is fluidically connected to the nozzle. Moreover, the pumping unit is adapted for pumping fluid from the fluid reservoir to the nozzle, and it comprises: (i) a riser pipe which is adapted to function as a piston in the pumping unit, and is firmly affixed to the user-facing side of the housing such as to be immobile relative to the housing; (ii) a hollow cylinder located upstream of the riser pipe, wherein the upstream end of the riser pipe is inserted in the cylinder such that the cylinder is longitudinally movable on the riser pipe; and (iii) a lockable means for storing potential energy when locked and for releasing the stored energy when unlocked, the means being arranged outside of, and mechanically coupled to, the cylinder such that unlocking the means results in a propulsive longitudinal movement of the cylinder towards the downstream end of the pumping unit.

The inhalation device according to the invention serves for the generation and delivery of a nebulised aerosol from medically active liquids, and in particular, of such aerosols which can be inhaled by a user or patient, e.g. in order to deliver a pharmacologically active ingredient contained in the liquid to the lungs of the user or patient.

In a further aspect, the invention provides a method for the generation of a nebulised aerosol of a medically active liquid (F) which comprises the steps of: (a) providing a hand-held inhalation device as defined in any one of the preceding claims, wherein the fluid reservoir of the inhalation device comprises a medically active liquid (F), and wherein the means for storing potential energy is in an unlocked state; (b) priming said inhalation device by causing the means for storing potential energy to alter its state from an unlocked state to a locked state, whereby the hollow cylinder performs a repulsive longitudinal movement on the riser pipe towards the upstream end of the pumping unit such as to allow medically active liquid to flow from the fluid reservoir into the hollow cylinder; and subsequently (c) actuating said inhalation device by causing the means for storing potential energy to become unlocked, whereby a propulsive longitudinal movement of the cylinder towards the downstream end of the pumping unit is effected and medically active liquid is ejected in a downstream direction from the hollow cylinder through the nozzle.

DETAILED DESCRIPTION OF THE INVENTION

Figure 1:
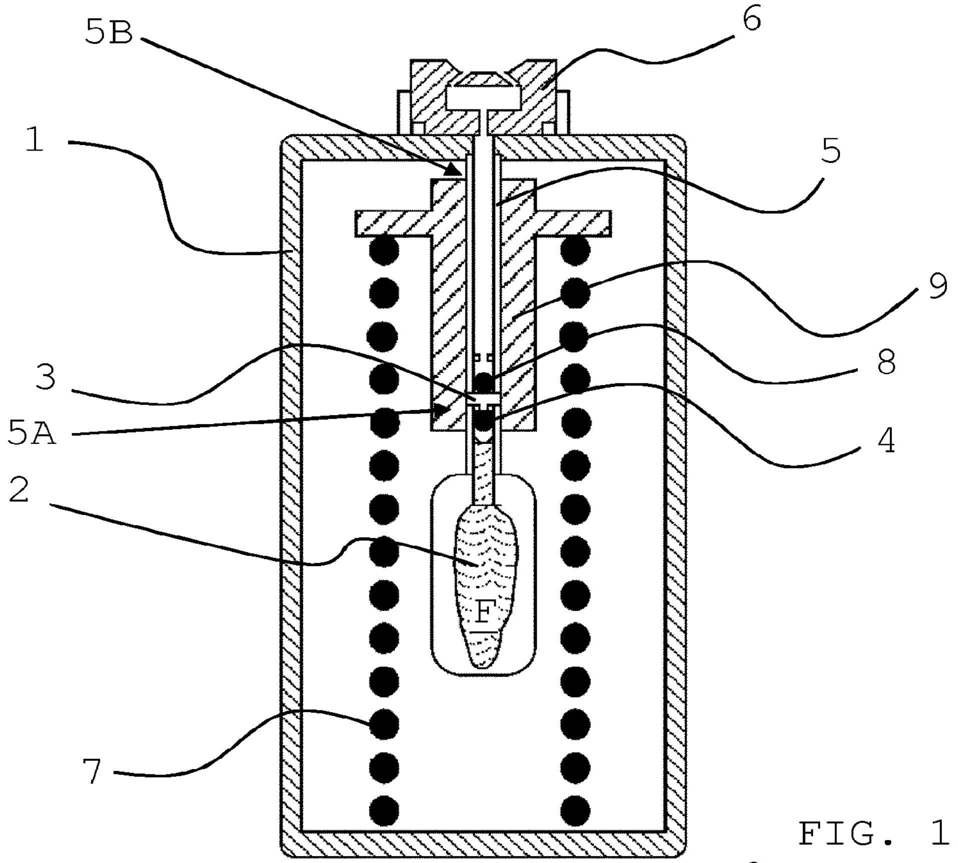
FIG. 1 shows schematically one preferred embodiment of the inhalation device according to the invention prior to its first use.

The present invention provides a hand-held inhalation device for delivering a nebulised medically active aerosol for inhalation therapy according to claim 1.

More specifically, the device comprises a housing having a user-facing side, an impingement-type nozzle for generating the nebulised aerosol by collision of at least two liquid jets, a fluid reservoir arranged within the housing, and a pumping unit which is also arranged within the housing. The nozzle is firmly affixed to the user-facing side of the housing such as to be immobile relative to the housing. The pumping unit has an upstream end that is fluidically connected to the fluid reservoir and a downstream end that is fluidically connected to the nozzle. Furthermore, the pumping unit is adapted for pumping fluid from the fluid reservoir to the nozzle, and it comprises a riser pipe which is adapted to function as a piston in the pumping unit, a hollow cylinder and a lockable means for storing potential energy. The riser pipe is firmly affixed to the user-facing side of the housing such as to be immobile relative to the housing. The hollow cylinder is located upstream of the riser pipe, and the upstream end of the riser pipe is inserted in the cylinder such that the cylinder is longitudinally movable on the riser pipe. The lockable means is capable of storing potential energy when locked and adapted for releasing the stored energy when unlocked. The means is arranged outside of, and mechanically coupled to, the cylinder in such a way that unlocking the means results in a propulsive longitudinal movement of the cylinder towards the downstream end of the pumping unit.

As used herein, a hand-held inhalation device is a mobile device which can be conveniently held in one hand and which is suitable for delivering a nebulised medically active aerosol for inhalation therapy. In order to be suitable for inhalation therapy, the device must be able to emit a medically active aerosol whose particle size is respirable, i.e. small enough to be taken up by the lungs of a patient or user. Typically, respirable particles have a mass median aerodynamic diameter of not more than about 10 μm, in particular not more than about 7 μm, or not more than about 5 μm, respectively. In this respect, inhalation devices are substantially different from devices that emits spray for oral or nasal administration, such as disclosed in US 2004/0068222 A1.

According to the invention, the inhalation device is capable of delivering a nebulised aerosol. As used herein, an aerosol is a system having at least two phases: a continuous phase which is gaseous and which comprises a dispersed liquid phase in the form of small liquid droplets. Optionally, the liquid phase may itself represent a liquid solution, dispersion, suspension, or emulsion.

Important for the generation of a nebulised aerosol is a suitable nozzle. According to the invention, the nozzle is of the impingement type. This means that the nozzle is adapted to emit at least two jets of liquid which are directed such as to collide and break up into small aerosol droplets. The nozzle is firmly affixed to the user-facing side of the housing of the inhalation device in such a way that it is immobile, or non-moveable, relative to the housing or at least relative to the side or part of the housing which faces the user (e.g. patient) when the device is used.

The fluid reservoir which is arranged within the housing is adapted to hold or store the medically active liquid from which the nebulised aerosol is generated and delivered by the inhalation device.

The pumping unit which is also arranged within the housing is adapted to function as a piston pump, also referred to as plunger pump, wherein the riser pipe functions as the piston, or plunger, which is longitudinally moveable within the hollow cylinder. The inner segment of the hollow cylinder in which the upstream end of the riser pipe moves forms a pumping chamber which has a variable volume, depending on the position of the riser pipe relative to the cylinder.

The hollow cylinder which provides the pumping chamber is fluidically connected with the fluid reservoir, either directly or indirectly, such as by means of an optional reservoir pipe (or reservoir pipe section). Similarly, the riser pipe, whose reservoir-facing, interior (upstream) end which can be received in the hollow cylinder, is fluidically connected at its downstream or exterior end to the nozzle in a liquid-tight manner, either directly or indirectly.

In this context, the expression “hollow cylinder” refers to a part or member which is hollow in the sense that it comprises an internal void which has a cylindrical shape, or which has a segment having a cylindrical space. In other words, and as is applicable to other types of piston pumps, it is not required that the external shape of the respective part or member is cylindrical. Moreover, the expression "hollow cylinder" does not exclude an operational state of the respective part or member in which the "hollow" space may be filled with material, e.g. with a liquid to be nebulised.

As used herein, a longitudinal movement is a movement along the main axis of the hollow cylinder, and a propulsive movement is a movement of a part in a downstream (or forward) direction.

Importantly, the riser pipe of the pumping unit of the inhalation device of the invention is arranged downstream of the cylinder, and it is firmly affixed to the user-facing side of the housing such as to be immobile relative to the housing or at least to the part of the housing which comprises the user-facing side of the housing. For the avoidance of doubt, firmly fixed means either directly or indirectly (i.e. via one or more connecting parts) fixed such as to prevent relative movement between the respective parts. As the nozzle is also immobile relative to the housing or the respective part of the housing, the riser pipe is also immobile relative to the nozzle, and the pumping action is effected by the longitudinal movement of the hollow cylinder. A propulsive movement of the cylinder, which is arranged in an upstream position relative to the riser pipe, results in a decrease of the volume of the pumping chamber, and a repulsive movement of the cylinder results in an increase of the volume. In other words, the riser pipe maintains its position relative to the housing, and the hollow cylinder can alter its position relative to the housing, and in particular, along a longitudinal axis of the same, such as to perform a piston-in-cylinder-type movement of the immobile riser pipe in the moveable cylindrical member.

This arrangement differs from other impingement-type inhalation devices which rely on a pumping unit whose riser pipe is in an upstream position and a cylindrical member in a downstream position wherein the riser pipe is moveable and the cylindrical member is fixed to the housing, as disclosed in US 2012/0090603 A1. A key advantage of the device of the invention is that the passage between pumping chamber and fluid reservoir can be designed with less restrictions with respect to its dimensions. It is e.g. possible to accommodate a significantly larger inlet valve (also referred to as check valve), which is easier to manufacture since it does not have to be contained within a narrow riser pipe. Instead, the invention allows the use of a check valve whose size is only restricted by the interior size of the housing or the dimensions of the means for storing potential energy. In other words, the diameters of the valve, the riser pipe and—if used—the reservoir pipe do not need to match each other. Furthermore, since no movable piston needs to be connected to the fluid reservoir, the component which provides the fluid connection to the reservoir can be designed independently of the moveable component, i.e. the hollow cylinder, allowing the individual parts to be adapted to suit their respective individual functions. In this respect, the invention provides for higher design flexibility because the moveable hollow cylinder, due to its robust structure and dimensions, provides better opportunities for designing a mechanically stable connection with the reservoir than would a less robust moveable riser pipe. Also, the connection between the hollow cylinder and the fluid reservoir can be designed with a larger diameter, such that higher flow velocities and fluid viscosities become feasible. Further, a support for the reservoir can be integrated into any component that comprises the cylinder. Additionally, any vent for pressure equilibration of the reservoir can be moved away from the reservoir body itself to (e.g.) a connector which forms an interface between reservoir and hollow cylinder, thus facilitating construction and avoiding the necessity to provide an essentially "open" reservoir body.

As mentioned, the lockable means for storing potential energy is adapted to store energy in its locked state and to release the stored energy when unlocked. The means is mechanically coupled to the hollow cylinder in such a way such that unlocking the means results in a propulsive longitudinal movement of the cylinder towards the downstream end of the pumping unit. During this movement, the internal volume of the cylinder, i.e. the volume of the pumping chamber, decreases. Vice versa, when the means for storing potential energy is in the locked state, the hollow cylinder is in its most upstream position in which the volume of the pumping chamber is largest. The locked state could also be considered a primed state. When the state of the means for storing energy is altered from the unlocked to the locked state, which could be referred to as priming the device, the hollow cylinder performs a repulsive longitudinal movement, i.e. from its most downstream position towards its most upstream position. A pumping cycle consists of two subsequent and opposing movements of the cylinder starting from its most downstream position to its most upstream (or primed) position and—driven by the means for storing potential energy that now releases its energy—back to its most downstream position.

In one of the preferred embodiments, the pumping unit is a high-pressure pumping unit and adapted to operate, or to expel fluid, at a pressure of at least about 50 bar. In other preferred embodiments, the operating pressure of the pumping unit is at least about 10 bar, or at least about 100 bar, or from about 2 bar to about 1000 bar, or from about 50 bar to about 250 bar, respectively. As used herein, the operating pressure is the pressure at which the pumping unit expels fluid, in particular a medically active liquid, such as an inhalable aqueous liquid formulation of a pharmacologically active ingredient, from its pumping chamber in a downstream direction, i.e. towards the nozzle. In this context, the expression "adapted to operate" means that the components of the pumping unit are selected with respect to the materials, the dimensions, the quality of the surfaces and the finish are selected such as to enable operation at the specified pressure.

Moreover, such high-pressure pumping unit implies that the means for storing potential energy is capable of storing and releasing a sufficient amount of energy to drive the propulsive longitudinal movement of the cylinder with such a force that the respective pressure is obtained.

The means for the storage of potential energy may be designed as tension or pressure spring. Alternatively, besides a metallic or plastic body, also a gaseous medium, or magnetic force utilizing material can be used as means for energy storage. By compressing or tensioning, potential energy is fed to the means. One end of the means is supported at or in the housing at a suitable location; thus, this end is essentially immobile. With the other end, it is connected to the hollow cylinder which provides the pumping chamber; thus, this end is essentially moveable. The means can be locked after being loaded with a sufficient amount of energy, such that the energy can be stored until unlocking takes place. When unlocked, the means can release the potential energy (e.g. spring energy) to the cylinder with the pumping chamber, which is then driven such as to perform a (in this case, longitudinal) movement. Typically, the energy release takes place abruptly, so that a high pressure can build up inside the pumping chamber before a significant amount of liquid is emitted, which results in a pressure decrease. In fact, during a significant portion of the ejection phase, an equilibrium exists of pressure delivered by the means for the storage of potential energy, and the amount of already emitted liquid. Thus, the amount of liquid remains essentially constant during this phase, which is a significant advantage to devices which use manual force of the user for the emission, such as the devices disclosed in documents US 2005/0039738 A1, US 2009/0216183 A1, US 2004/0068222 A1, or US 2012/0298694 A1, since manual force depends on the individual user or patient and is very likely to vary largely during the ejection phase, resulting in inhomogeneous droplet formation, size, and amount. In contrast to the prior art, the means according to the invention ensures that the inhalation device delivers highly reproducible results.

The means for storing potential energy may also be provided in the form of a highly pressurized gas container. By suitable arrangement and repeatable intermittent activating (opening) of the same, part of the energy which is stored inside the gas container can be released to the cylinder. This process can be repeated until the remaining energy is insufficient for once again building up a desired pressure in the pumping chamber. After this, the gas container must be refilled or exchanged.

In one of the preferred embodiments, the means for storing potential energy is a spring having a load of at least 10 N in a deflected state. In a particularly preferred embodiment, the means for storing potential energy is a compression spring made of steel having a load from about 1 N to about 500 N in its deflected state. In other preferred embodiments, the compression spring from steel has a load from about 2 N to about 200 N, or from about 10 N to about 100 N, in its deflected state.

The inhalation device according to the invention is preferably adapted to deliver the nebulised medically active aerosol in a discontinuous manner, i.e. in the form of discrete units, wherein one unit is delivered per pumping cycle. In this aspect, the device differs from commonly known nebulisers such as jet nebulisers, ultrasonic nebulisers, vibrating mesh nebulisers, or electrohydrodynamic nebulisers which typically generate and deliver a nebulised aerosol continuously over a period of several seconds up to several minutes, such that the aerosol requires a number of consecutive breathing manoeuvres in order to be inhaled by the patient or user. Instead, the inhalation device of the invention is adapted to generate and emit discrete units of aerosol, wherein each of the units corresponds to the amount (i.e. volume) of fluid (i.e. medically active liquid) which is pumped by the pumping unit in one pumping cycle into the nozzle where it is immediately aerosolised and delivered to the user or patient. Vice versa, the amount of liquid pumped by the pumping unit in one pumping cycle determines the amount of the pharmacologically active agent which the patient receives per dosing. It is therefore highly important with respect to achieving the desired therapeutic effect that the pumping unit operates precisely, reliably and reproducibly. The inventors have found that the inhalation device incorporating the pumping unit as described herein is particularly advantageous in that it does exhibit high precision and reproducibility.

In one preferred embodiment, a single dose of the medication (i.e. of the nebulised aerosol of the medically active liquid) is contained in one unit, i.e. in the volume that is delivered from the pumping unit to the nozzle for aerosol generation in one single pumping cycle. In this case, the user or patient will prime and actuate the device only once, and inhale the released aerosol in one breathing manoeuvre, per dosing (i.e. per dosing event).

In another preferred embodiment, a single dose of the medication consists of two units of the aerosol, and thus requires two pumping cycles. Typically, the user or patient will prime the device, actuate it such as to release and inhale a unit of the aerosol, and then repeat the procedure. Alternatively, three or more aerosol units may constitute a single dosing.

The volume of fluid (e.g. of medically active liquid) that is pumped by the pumping unit in one pumping cycle is preferably in the range from about 2 to about 150 μl. In particular, the volume may range from about 0.1 to about 1000 μl, or from about 1 to about 250 μl, respectively. This volume ranges are nearly the same as the volume of liquid phase that is contained in one unit of aerosol generated by the inhalation device, perhaps with minor differences due to minute losses of liquid in the device.

In another preferred embodiment, the pumping unit comprises an inlet valve, also referred to as a check valve or inlet check valve, positioned in the hollow cylinder. According to this embodiment, the interior space of the hollow cylinder, i.e. the pumping chamber, is fluidically connected with the fluid reservoir via the inlet check valve. The inlet valve allows the inflow of liquid into the pumping chamber, but prevents the backflow of liquid towards, or into, the fluid reservoir. The position of the inlet valve may be at or near the upstream end of the cylinder such as to make nearly the entire internal volume of the hollow cylinder available for functioning as the pumping chamber. Alternatively, it may be more centrally located along the (longitudinal) main axis of the hollow cylinder such as to define an upstream segment and a downstream segment of the cylinder, the upstream segment being upstream of the inlet valve and the downstream segment being downstream of the valve. In this case the pumping chamber is located in the downstream segment.

As mentioned, one of the advantageous effects of the invention is that an inlet valve having relatively large dimensions may be accommodated in this position, i.e. at the upstream end of the pumping chamber. This is particularly beneficial as it allows for large dimensions of the fluid conduit(s) within the valve, thus enabling high fluid velocities which translate into a rapid filling of the pumping chamber during the priming of the inhalation device. Moreover, the use of liquids having a higher viscosity than ordinary liquid formulations for inhalation, such as highly concentrated solutions of soluble active ingredients, become feasible for inhalation therapy.

According to a further preferred embodiment, the inlet valve is adapted to open only when the pressure difference between the upstream and the downstream side of the valve, i.e. the fluid reservoir side and the pumping chamber side, is above a predefined threshold value, and remains closed as long as the pressure difference is below the threshold value. "Pressure difference" means that, irrespective of the absolute pressure values, only the relative pressure difference between the two sides is relevant for determining whether the valve blocks or opens. If, for example, the pressure on the upstream (reservoir) side is already positive (e.g. 1.01 bar due to thermal expansion), but the pressure on the downstream (pumping chamber) side is ambient pressure (1.0 bar, no activation of the device), the pressure difference (here: 0.01 bar) is below the threshold value (e.g. 20 mbar), which allows the valve to stay closed even when subject to a positive pressure in opening direction. This means that the check valve remains closed until the threshold pressure is met, thus keeping the passage between reservoir and pumping chamber safely shut e.g. when the inhalation device is not in use. Examples for threshold pressure differences are in the range of 1 to 1000 mbar, and more preferably between about 10 and about 500 mbar, or between about 1 and about 20 mbar.

When actuating the inhalation device, as the means for storing potential energy alters its state from a locked state to an unlocked state, energy is released which effects the cylinder to perform its propulsive longitudinal movement, significant pressure is built up in the pumping chamber. This generates a marked pressure difference (due to a high pressure in the pumping chamber and a substantially lower pressure in the fluid reservoir) which exceeds the threshold value of the pressure difference, so that the check valve opens and allows the pressure chamber to become filled with liquid from the reservoir.

A valve type that may be designed to operate with such a threshold pressure difference is a ball valve pre-loaded with a spring. The spring pushes the ball into its seat, and only if the pressure acting against the spring force exceeds the latter, the ball valve opens. Other valve types which—depending on their construction—may operate with such a threshold pressure difference are duckbill valves or flap valves.

The advantage of such a valve operating with a threshold pressure difference is that the reservoir can be kept closed until active use is being made of the inhalation device, thus reducing unwanted splashing of reservoir liquid during device transport, or evaporation during long-term storage of the device.

In a further preferred embodiment, the inhalation device according to the invention further comprises an outlet valve inside the riser pipe, or at an end of the riser pipe, for avoiding a return flow of liquid or air from the riser pipe into the hollow cylinder. In many cases, the use of such outlet valve will prove to be advantageous. Typically, the downstream end of the riser pipe is located close to the nozzle. The nozzle is in fluidic communication with the outside air. After emitting, in aerosolised form, the amount of liquid which is delivered from the pumping unit through the nozzle, driven by the propulsive longitudinal movement of the cylinder, the pumping chamber must be refilled. For this purpose, it slides back on the riser pipe into its previous upstream position (i.e. performs a repulsive longitudinal movement), so that the interior volume of the pumping chamber increases. Along with this, a negative pressure (sometimes also referred to as "underpressure") is generated inside the pumping chamber which causes liquid to be sucked into the pumping chamber from the fluid reservoir which is located upstream of the pumping chamber. However, such negative pressure may also propagate downstream through the riser pipe up to the outside of the nozzle and could lead to air being sucked into the device through the nozzle, or nozzle openings, respectively. This problem can be avoided by providing an outlet valve, also referred to as outlet check valve, which opens towards the nozzle openings and blocks in the opposite direction.

Optionally, the outlet valve is of a type that blocks below (and opens above) a threshold pressure difference as described in the context of the inlet valve above. If a ball valve with a spring is used, the spring force must be directed against the pumping chamber such that when the difference between the interior pressure of the pumping chamber and the ambient pressure exceeds the threshold pressure difference value, the outlet valve opens. The advantages of such a valve correspond to the respective aforementioned advantages.

As mentioned, the outlet valve may be positioned within the riser pipe. Alternatively, the inhalation device comprises an outlet valve which is not integrated within the riser pipe, but positioned at or near one of the ends of the riser pipe, in particular at or near its downstream end, e.g. in a separate connector between the riser pipe and the nozzle. This embodiment may be advantageous in certain cases, e.g. if there is a need for a riser pipe with a particularly small diameter which makes the integration of a valve difficult. By accommodating the outlet valve downstream of the riser pipe, a valve with a relatively large diameter may be used, thus simplifying the requirements for the valve design.

In a further alternative embodiment, the outlet valve is absent. This embodiment may be feasible as the fluid channels of an impingement-type nozzle may have relatively small cross sections, resulting in only minor or very slow back flow at the given pressure conditions during the priming of the device. If the amount of backflow is considered acceptable in view of a particular product application, the inhaler design may be simplified by avoiding the outlet valve.

In any case, whether the inhalation device is designed with or without an outlet valve, all other options and preferences described with respect to other device features are applicable to both of these alternative embodiments.

In a further preferred embodiment, the inhalation device according to the invention comprises a fluid reservoir which is firmly attached to the hollow cylinder such as to be moveable together with the hollow cylinder inside the housing. This means that in each ejection phase of the pumping cycle, the fluid reservoir moves together with the hollow cylinder from an initial ("upstream") position, in which the pumping chamber has its maximum interior volume, towards an end ("downstream") position, in which the volume of the pumping chamber is minimal; and during the subsequent "priming" step, the fluid reservoir returns together with the hollow cylinder to their initial ("upstream") position.

As used herein, the expression "firmly attached" includes both permanent and nonpermanent (i.e. releasable) forms of attachment. Moreover, it includes direct and indirect (i.e. via one or more connecting parts) types of attachment. At the same time, as mentioned above, "firmly attached" means that the respective parts are fixed to each other in such a way as to substantially prevent their movement relative to each other. In other words, two parts that are firmly attached to each other may only be movable together, and with respect to each other, they are non-movable or immobile.

One of the advantages of this embodiment wherein the fluid reservoir is firmly attached to the hollow cylinder is that it provides the smallest possible dead volume between the reservoir and the pumping chamber.

According to an alternative embodiment, the fluid reservoir is fluidically connected to the hollow cylinder by means of a flexible tubular element, and firmly attached to the housing. According to this embodiment, the reservoir is not firmly attached to the hollow cylinder and does not move along with it when the cylinder performs its longitudinal movements. Instead, it is firmly, but optionally detachably, directly or indirectly, attached to the housing or to a part of the housing. One advantage of this embodiment is that the energy which is abruptly released upon unlocking the means for storing potential energy solely acts on the hollow cylinder and not on the fluid reservoir. This may be particularly advantageous in cases in which the fluid reservoir in its initial (fully filled state) at the beginning of its usage has a relatively large mass which decreases over use. A higher acceleration of the hollow cylinder would translate into a higher pressure in the pumping chamber.

For the avoidance of doubt, all other options and preferences described herein-above and below with respect to other device features are applicable to both of these alternatives, i.e. regardless of whether the fluid reservoir is firmly attached to the hollow cylinder or not.

In one embodiment, the fluid reservoir is designed to be collapsible, such as by means of a flexible or elastic wall. The effect of such design is that upon repeated use of the device which involves progressive emptying of the reservoir, the flexible or elastic wall buckles or folds such as to reduce the internal volume of the reservoir, so that the negative pressure which is necessary for extraction of a certain amount of liquid is not required to increase substantially over the period of use. In particular, the reservoir may be designed as a collapsible bag. The advantage of a collapsible bag is that the pressure inside the reservoir is almost independent of the filling level, and the influence of thermal expansion is almost negligible. Also, the construction of such a reservoir type is rather simple and already well established.

A similar effect can be achieved with a rigid container which has a moveable bottom (or wall) by means of which the interior volume of the reservoir can also be successively reduced.

Further specific and advantageous embodiments of the inhalation device provided by the invention are as follows:

(a) An inhalation device for medically active liquids for generation of an aerosol, comprising a housing, inside this housing a reservoir for storing a liquid, a pumping device with a pumping chamber for generation of a pressure inside said pumping chamber, wherein the pumping chamber is fluidically connected with the reservoir via a check valve which blocks in direction of the reservoir, a riser pipe which can be received with at least one reservoir-facing, interior end in said pumping chamber, and a nozzle which is connected liquid-tight to an exterior end of the riser pipe, wherein the interior volume of the pumping chamber is changeable by means of relative motion of the pumping chamber to the riser pipe, characterized in that the riser pipe is immobile and firmly attached to the housing or to the nozzle, and the pumping chamber is moveable relative to the housing or to the nozzle.

(b) The inhalation device of embodiment (a), further comprising a means for the storage of potential energy, the device being coupled to the pumping chamber and being lockable in a loaded position, wherein upon unlocking, the stored energy is transformable into a motion of the pumping chamber.

(c) The inhalation device of embodiment (a) or (b), wherein the check valve is adapted to open only when the pressure difference between an upstream and a downstream side of the check valve is above a predefined threshold value.

(d) The inhalation device of any one of embodiments (a) to (c), further comprising an outlet valve inside the riser pipe for avoiding a return flow of liquid or air towards the exterior end of the same.

(e) The inhalation device of any one of embodiments (a) to (d), further comprising an outlet valve between riser pipe and nozzle for avoiding a return flow of liquid or air towards the exterior end of the same.

(f) The inhalation device of any one of embodiments (a) to (e), wherein the reservoir is firmly attached to the pumping chamber and thus moveable inside the housing.

(g) The inhalation device of any one of embodiments (a) to (e), wherein the reservoir is connected to the pumping chamber by means of a flexible element, and firmly attached to the housing.

(h) The inhalation device according to any one of embodiments (a) to (g), wherein the reservoir is designed as a collapsible bag.

In a further aspect, the invention provides a method for the generation of a nebulised aerosol of a medically active liquid. The method may involve the use of the inhalation device as described herein-above, in any of its embodiments. Therefore, all options and preferences described above with respect to the features of the inhalation are also applicable to the method provided according to the invention.

In particular, the method comprises the steps of:

(a) providing a hand-held inhalation device as defined in any one of the preceding claims, wherein the fluid reservoir of the inhalation device comprises a medically active liquid, and wherein the means for storing potential energy is in an unlocked state;

(b) priming said inhalation device by causing the means for storing potential energy to alter its state from an unlocked state to a locked state, whereby the hollow cylinder performs a repulsive longitudinal movement on the riser pipe towards the upstream end of the pumping unit such as to allow medically active liquid to flow from the fluid reservoir into the hollow cylinder; and subsequently (c) actuating said inhalation device by causing the means for storing potential energy to become unlocked, whereby a propulsive longitudinal movement of the cylinder towards the downstream end of the pumping unit is effected and medically active liquid is ejected in a downstream direction from the hollow cylinder through the nozzle.

According to the invention, during the movement of the hollow cylinder relative to the housing and to the nozzle, the riser pipe stays immobile, while the cylinder which provides the pumping chamber alters its relative position. In other words, the pumping chamber is moveably supported within the housing, whereas riser pipe and nozzle are firmly and immovably, or stationary, attached to the housing and/or nozzle.

In that it relies on the use of a particularly advantageous inhalation device, the method provides an improvement to the methods known from the art, wherein the component corresponding to the riser pipe, namely the hollow piston, is moveable with respect to housing and nozzle, and the riser pipe is stationary.

According to further preferred embodiments, the described method is carried out by means of an inhalation device that provides one, several, or all of the aforementioned features, such as: a reservoir, being firmly attached to the hollow cylinder or being firmly attached to the housing, and optionally being provided as a collapsible bag; an inlet check valve, optionally operable by using a threshold pressure difference; a means for the storage of potential energy such as e.g. a spring; a locking device; and an outlet valve, being e.g. arranged inside the riser pipe or between riser pipe and nozzle. For explanations regarding the respective operation of said features, reference is made to the sections of the description that relate to the respective device features.

According to a further specific and advantageous embodiment, the invention provides a method for the generation of an aerosol of a medically active liquid by means of an inhalation device, the device comprising a housing, a pumping device with a pumping chamber, a riser pipe, and a nozzle, by performing the steps of moving an interior end of the riser pipe into the interior volume of the pumping chamber such that the latter is reduced and a pressure of a liquid contained within this volume is increased; and ejecting said liquid through an exterior end of said riser pipe and the nozzle such that a spray is formed;

characterized in that during said motion, with regard to housing and/or nozzle, said riser pipe stays immobile, while said pumping chamber alters its relative position.

As has been shown above, the invention solves the drawbacks of the known art. It also allows for the nebulisation and delivery of aerosols from liquids of higher viscosities in a short time, and with high reproducibility.

DETAILED DESCRIPTION OF THE DRAWINGS

In FIG. 1, one of the preferred embodiments of the inhalation device according to the invention is depicted schematically and not-to-scale. FIG. 1 shows the situation prior to first use.

The inhalation device comprises a housing (1), which is preferably shaped and dimensioned such that it can be held with one hand and can be operated by one finger, e.g. a thumb or index finger (not shown). A fluid reservoir (2) for the storage of a medically active liquid (F) is located inside the housing (1). The depicted reservoir (2) is designed to be collapsible so that in the course of the emptying of the reservoir by the repeated use of the device, the soft or elastic walls deform such that the negative pressure required for withdrawing liquid from the reservoir remains substantially constant over time. A similar effect could be achieved with a rigid container that has a movable bottom by means of which the interior volume of the reservoir can also be successively be reduced (not shown).

Furthermore, the inhalation device comprises a pumping unit with a hollow cylinder (9) within the housing (1) which forms a pumping chamber (3) for the generation of the desired pressure which is necessary for emitting liquid (F) and nebulising the same. The pumping unit may also comprise further components not depicted in the drawing, such as a push button, locking device, etc.

As a means for the storage of potential energy (7), a spring is provided which is coupled with one end (upwards directed, or downstream) to the cylinder (9) and which is supported at the housing (1) (lower part of the figure).

The inhalation device further comprises a riser pipe (5) with at least one reservoir-facing, or upstream, interior end (5A) which can be received in said cylinder (9). In other words, riser pipe (5) can be at least partially pushed into hollow cylinder (9), resulting in a decrease of the interior volume of pumping chamber (3). The term "interior volume" describes the volume of the space which extends from the reservoir-facing inlet of the cylinder (9) to the place where the interior end (5A) of the riser pipe (5) is located. In the depicted situation, riser pipe (5) is almost entirely contained in the cylinder (9). As a result, the interior volume of the pumping chamber (3), situated between inlet valve (4) and the interior end (5A) of riser pipe (5), is at a minimum.

Preferably, the section (or segment) of the hollow cylinder (9) which serves as, or accommodates, the pumping chamber (3) and which receives the riser pipe (5) exhibits a circular inner cross-section whose diameter relatively closely (e.g. except for a small gap) matches the diameter of the circular outer cross-section of the corresponding segment of the riser pipe (5). Of course, other (e.g. non-circular) cross section shapes are possible as well.

According to the depicted embodiment, inlet valve (4) is arranged between reservoir (2) and inlet of the pumping chamber (3) formed by the cylinder (9).

Furthermore, the inhalation device comprises a nozzle (6) which is connected liquid-tight to the exterior (or downstream) end (5B) of the riser pipe (5). Nozzle (6) is an impingement-type nozzle for generating the nebulised aerosol by collision of at least two liquid jets. Preferably, the cross sections of the liquid-containing channels are relatively small, typically in the region of microns.

Also depicted is an optional outlet valve (8) inside the riser pipe (5) for avoiding a backflow of liquid or air into the exterior end (5B) of the same from the outside. Outlet valve (8) is arranged in the interior end (5A) of riser pipe (5). Liquid (F) can pass outlet valve (8) in direction of nozzle (6), but outlet valve (8) blocks any undesired backflow in the opposite direction.

As can be seen in FIG. 1, riser pipe (5) is designed immobile with respect to the housing (1), and firmly attached to housing (1), indicated by the connection in the region of exterior end (5B) with housing (1). Riser pipe (5) is also firmly attached to nozzle (6), which in turn is attached to housing (1) as well. In contrast, the hollow cylinder (9) providing the pumping chamber (3) is designed to be moveable with respect to housing (1) and nozzle (6). The benefits of this design have been explained; reference is made to the respective sections of the description above.

Figure 2:
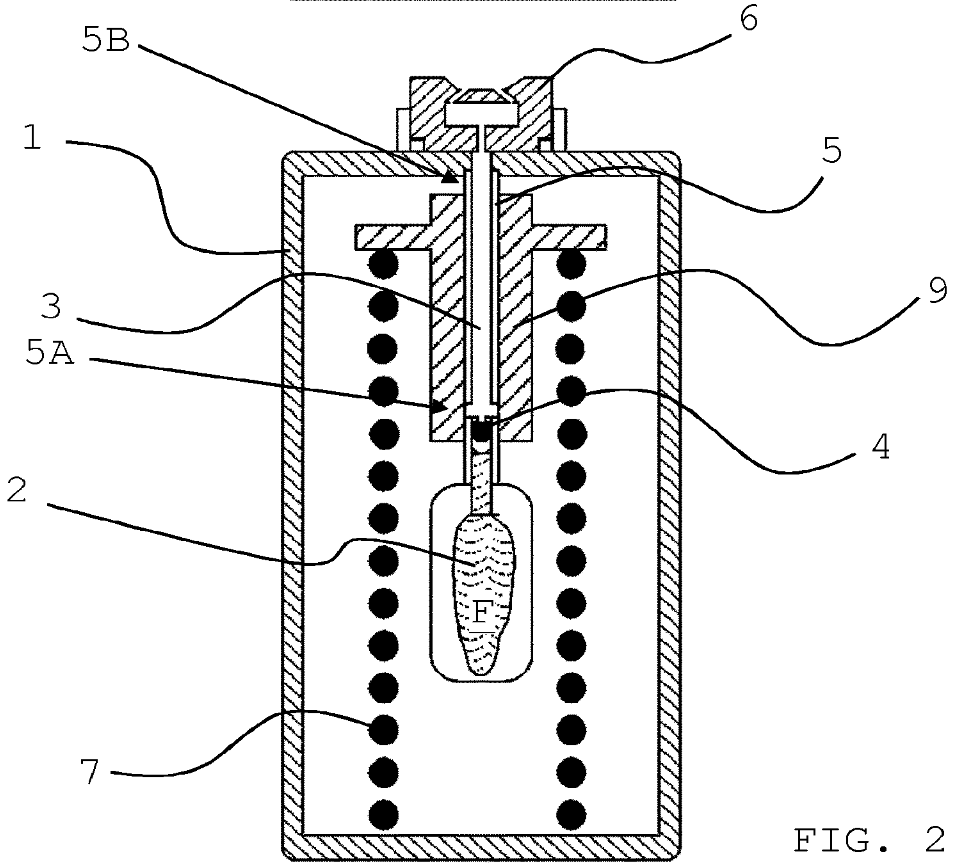
FIG. 2 shows a device similar to the one of FIG. 1, but without an outlet valve.

Referring to FIG. 2, a device similar to the one of FIG. 1 is depicted. However, the embodiment shown in FIG. 2 lacks the (optional) outlet valve (8). All other components are present, and also the function is comparable. In this embodiment, pumping chamber (3) extends from downstream of the valve (4) up to nozzle (6), which is the location where the fluidic resistance increases significantly. In an alternative embodiment having a particularly small inner diameter of riser pipe (5), pumping chamber (3) extends only from downstream of the valve (4) up to upstream interior end (5A) of riser pipe (5).

Figure 3:
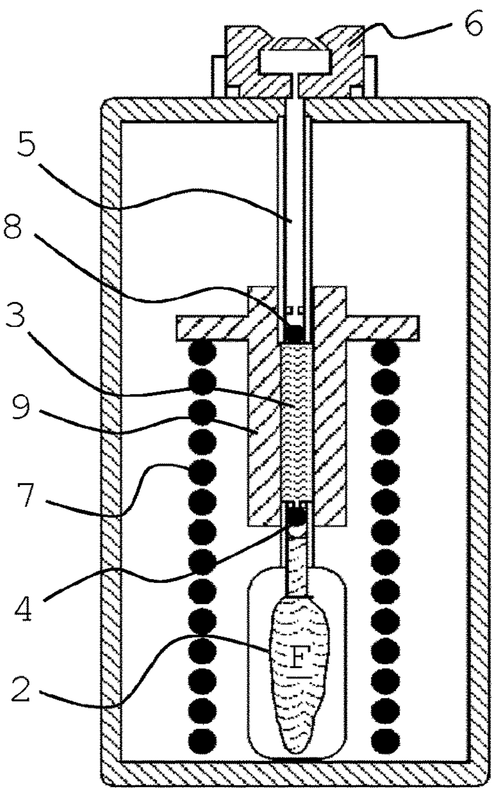
FIG. 3 shows the embodiment of FIG. 1 with a filled pumping chamber.

FIG. 3 shows the embodiment of FIG. 1 with a filled pumping chamber. The hollow cylinder (9) has been moved to its most upstream position, thereby loading the means for the storage of potential energy (7). Outlet valve (8) is closed due to negative pressure inside pumping chamber (3), and the inlet valve (4) is open towards the fluid reservoir (2). Increasingly collapsing walls of reservoir (2) allow the internal pressure in the reservoir (2) to remain nearly constant, while the pressure inside the pumping chamber (3) drops because of the propulsive longitudinal motion of the hollow cylinder (9), thus increasing the volume of pumping chamber (3). As a result, the pumping chamber (3) has been filled with liquid (F) from the reservoir (2).

Figure 4:
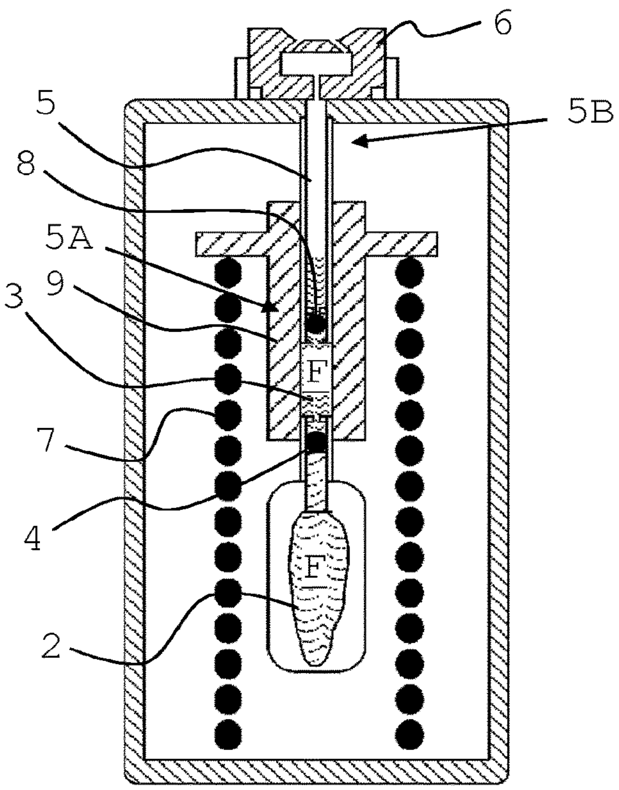
FIG. 4 shows the situation during the first actuation of the device.

In FIG. 4, the situation after the first actuation of the inhalation device of FIG. 1 is shown. The means for the storage of potential energy (7) has been released from the loaded position as shown in FIG. 3. It pushes the cylinder (9) in a downstream direction such as to slide over the riser pipe (5). The interior end (5A) of the riser pipe (5) has come closer to the inlet check valve (4) which is now closed. As a result, the pressure inside the pumping chamber (3) rises and keeps the inlet valve (4) closed, but opens outlet valve (8). Liquid (F) flows from the riser pipe (5) through its exterior end (5B) towards nozzle (6).

Figure 5:
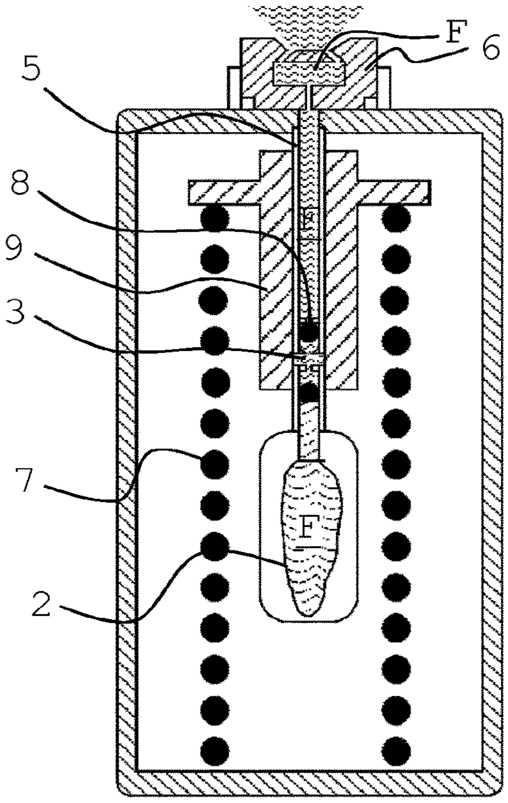
FIG. 5 shows the situation at the end of the first actuation.

FIG. 5 shows the device of FIG. 1 in the situation at the end of the aerosol emission phase. The means for the storage of potential energy (7) is in its most relaxed end position (spring fully extended). Also, the hollow cylinder (9) has been pushed almost entirely onto riser pipe (5) such that the interior volume of pumping chamber (3) has reached its minimum. Most of the liquid (F) previously contained in the pumping chamber (3) has passed outlet valve (8) into the main segment of the riser pipe (5). Some liquid (F) has been pushed towards, and though, nozzle (6), where nebulisation takes place, such that a nebulised aerosol is emitted towards the user or patient.

Figure 6:
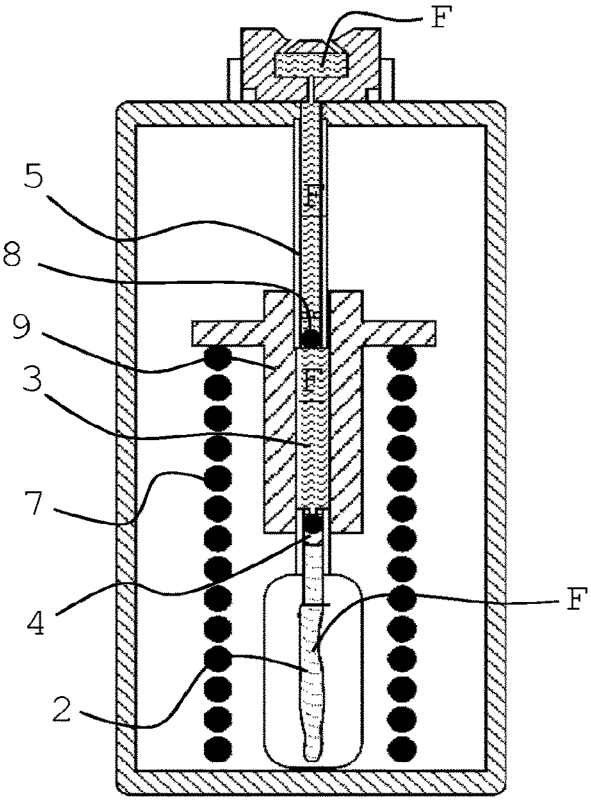
FIG. 6 shows the situation after re-filling the pumping chamber.

In FIG. 6, the device of FIG. 1 in the situation after re-filling the pumping chamber is depicted. The hollow cylinder (9) has been moved (repulsively) in an upstream direction, thus increasing the volume of the pumping chamber (3) provided by the cylinder (9). The means for the storage of potential energy (7) has been loaded (spring compressed). During movement of cylinder (9) away from the nozzle (6), an negative pressure has been generated in the pumping chamber (3), closing outlet valve (8) and opening the inlet check valve 4. As a result, further liquid (F) is drawn from reservoir (2) into the pumping chamber (3). The inhalation device's pumping chamber (3) is filled again and ready for the next ejection of liquid (F) by releasing the spring.

LIST OF REFERENCES

1 Housing
2 Fluid reservoir, reservoir
3 Pumping chamber
4 Inlet valve
5 Riser pipe
5A Interior end
5B Exterior end
6 Nozzle
7 Means for storing potential energy, means
8 Outlet valve
9 Hollow cylinder, cylinder
F Liquid, fluid

What is claimed is:

1. An inhalation device for delivering a nebulized medically active aerosol for inhalation therapy, the inhalation device comprising:
- a housing configured to receive a fluid reservoir therein;
- an impingement-type nozzle fixed to the housing; and
- a pumping unit located in the housing, the pumping unit comprising:
  - a riser pipe that is immovably fixed to the housing and in fluid communication with the impingement-type nozzle; and
  - a hollow cylinder with the riser pipe at least partially inserted into an interior of the hollow cylinder, the hollow cylinder longitudinally translatable along an outer circumference of the riser pipe and configured to be in fluid communication with the fluid reservoir,
  - an internal space of the riser pipe and hollow cylinder defining a variable volume of the pumping unit, the variable volume of the pumping unit variably based on a longitudinally translational position of the hollow cylinder along the outer circumference of the riser pipe; and
  - a spring mechanically coupled to the hollow cylinder, the spring configured to vary the variable volume of the pumping unit by changing the longitudinally translational position of the hollow cylinder along the outer circumference of the riser pipe.

2. The inhalation device according to claim 1, the pumping unit further comprising:
- an inlet valve located at an upstream end of the hollow cylinder, the inlet valve configured to prevent upstream backflow.

3. The inhalation device according to claim 2, wherein the inlet valve is configured to open when a pressure difference between an upstream side of the inlet valve and a downstream side of the inlet valve is greater than a predefined threshold value, the predefined threshold value in a range from 1 to 1000 mbar.

4. The inhalation device according to claim 1, the pumping unit further comprising:
- an outlet valve located in the riser pipe, the outlet valve configured to prevent upstream backflow.

5. The inhalation device according to claim 1, wherein the hollow cylinder is configured to receive the fluid reservoir for attachment, with the fluid reservoir firmly attached to the hollow cylinder and longitudinally translatable along with the hollow cylinder within the housing.

6. The inhalation device according to claim 1, wherein
- the housing is configured to receive the fluid reservoir for attachment with the fluid reservoir firmly attached to the housing;
- the hollow cylinder further comprising a flexible tubular element configured to be in fluid communication with the fluid reservoir.

7. The inhalation device according to claim 1, wherein
- the fluid reservoir is configured to store a medically active liquid;
- the pumping unit is configured to receive a discrete unit of the medically active liquid, and via the spring pressurize the medically active liquid and to expel the discrete unit of medically active liquid via the nozzle to generate the nebulized medically active aerosol.

8. The inhalation device according to claim 7, wherein the spring is configured to pressurize the discrete unit of the medically active liquid in the pumping unit at at least 50 bar.

9. The inhalation device according to claim 7, wherein the discrete unit of medically active liquid has a volume in a range from 2 to 150 μl.

10. The inhalation device according to claim 7, wherein the fluid reservoir comprises a collapsible bag.

11. An inhalation device for delivering a nebulized medically active aerosol for inhalation therapy, the inhalation device comprising:
- a housing configured to receive a fluid reservoir therein;
- an impingement-type nozzle fixed to the housing; and
- a pumping unit located in the housing, the pumping unit comprising:
  - a riser pipe that is immovably fixed to the housing and in fluid communication with the impingement-type nozzle; and
  - a hollow cylinder with the riser pipe at least partially inserted into an interior of the hollow cylinder, the hollow cylinder longitudinally translatable along an outer circumference of the riser pipe and configured to be in fluid communication with the fluid reservoir,
  - the hollow cylinder comprising an inlet check valve configured to prevent upstream backflow,
  - an internal space of the riser pipe and hollow cylinder defining a variable volume of the pumping unit, the variable volume of the pumping unit variably based on a longitudinally translational position of the hollow cylinder along the outer circumference of the riser pipe; and a spring mechanically coupled to the hollow cylinder, the spring configured to vary the variable volume of the pumping unit by changing the longitudinally translational position of the hollow cylinder along the outer circumference of the riser pipe.

12. The inhalation device according to claim 11, wherein the inlet check valve is located at an upstream end of the hollow cylinder.

13. The inhalation device according to claim 11, wherein the inlet check valve is located centrally within the hollow cylinder dividing the hollow cylinder in an upstream segment and a downstream segment, and the variable volume of the pumping unit is defined by the internal space of the riser pipe and the downstream segment of the hollow cylinder.

14. The inhalation device according to claim 11, wherein a diameter of the inlet check valve is larger than an internal diameter of the riser pipe.

15. The inhalation device according to claim 11, wherein the inlet check valve is configured to open when a pressure difference between an upstream side of the inlet check valve and a downstream side of the inlet check valve is greater than a predefined threshold value.

16. The inhalation device according to claim 15, wherein the predefined threshold value is in a range from 1 to 20 mbar.

17. The inhalation device according to claim 11, wherein, the inlet check valve is a ball valve.

18. The inhalation device according to claim 11, wherein, the inlet check valve is a duck bill valve.

19. The inhalation device according to claim 11, wherein, the inlet check valve is a flap valve.

20. The inhalation device according to claim 11, the pumping unit further comprising:

an outlet valve located in the riser pipe, the outlet valve configured to prevent upstream backflow.

* * * * *